(12) United States Patent
Domínguez Chávez et al.

(10) Patent No.: US 10,301,316 B2
(45) Date of Patent: May 28, 2019

(54) SOLID FORMS OF SITAGLIPTIN

(71) Applicant: ALPARIS, S.A. DE C.V., Mexico City (MX)

(72) Inventors: Jorge Guillermo Domínguez Chávez, Veracruz (MX); Karina Mondragón Vásquez, Veracruz (MX); Juan Pablo Senosiain Peláez, Mexico City (MX)

(73) Assignee: ALPARIS, S.A. DE C.V., Mexico City (MX)

( * ) Notice: Subject to any disclaimer, the term of this patent is extended or adjusted under 35 U.S.C. 154(b) by 0 days.

(21) Appl. No.: 15/835,827

(22) Filed: Dec. 8, 2017

(65) Prior Publication Data

US 2018/0170937 A1 Jun. 21, 2018

(30) Foreign Application Priority Data

Dec. 8, 2016 (MX) .................. MX/a/2016/016260

(51) Int. Cl.
*A61K 31/4985* (2006.01)
*A61P 3/10* (2006.01)
*C07D 487/04* (2006.01)
*C07C 65/03* (2006.01)

(52) U.S. Cl.
CPC ............ *C07D 487/04* (2013.01); *C07C 65/03* (2013.01); *A61P 3/10* (2018.01)

(58) Field of Classification Search
CPC .................... A61K 31/4985; C07D 487/04
See application file for complete search history.

(56) References Cited

U.S. PATENT DOCUMENTS

| 6,699,871 B2 | 3/2004 | Edmondson et al. |
| 7,326,708 B2 | 2/2008 | Cypes et al. |
| 9,108,972 B2 * | 8/2015 | Pandey ................ C07D 487/04 |
| 2014/0081026 A1 | 3/2014 | Rasparini et al. |
| 2014/0350023 A1 | 11/2014 | Jayachandra et al. |
| 2015/0051213 A1 | 2/2015 | Jayachandra et al. |

FOREIGN PATENT DOCUMENTS

| WO | 2005072530 A1 | 8/2005 |
| WO | 2009085990 A2 | 7/2009 |
| WO | 2010000469 A2 | 1/2010 |
| WO | 2010092090 A2 | 8/2010 |
| WO | 2012131005 A1 | 10/2012 |
| WO | 2012147092 A2 | 11/2012 |
| WO | 2013001457 A1 | 1/2013 |
| WO | 2013054364 A2 | 4/2013 |
| WO | 2015114657 A2 | 8/2015 |
| WO | 2016046679 A1 | 3/2016 |

* cited by examiner

*Primary Examiner* — Brenda L Coleman
(74) *Attorney, Agent, or Firm* — Saul Ewing Arnstein & Lehr LLP; Debora Plehn-Dujowich; Domingos J. Silva

(57) ABSTRACT

New amorphous solid phases of sitagliptin with derivatives of hydroxybenzoic acids, dihydroxybenzoic acids and trihydroxybenzoic acids as coformers; the obtained new solid phases possess enhanced pharmaceutical properties such as enhanced solubility and higher dissolution rate, as compared to the sitagliptin phosphate monohydrate, and they are also stable under ambient conditions.

4 Claims, 14 Drawing Sheets

SOLID FORMS OF SITAGLIPTIN

CROSS-REFERENCE TO RELATED APPLICATIONS

This application claims priority under 35 U.S.C. § 119(b) to Mexican Application No. MX/a/2016/016260, filed Dec. 8, 2016, the entire disclosure of which is incorporated herein by reference.

FIELD OF THE INVENTION

The present invention refers to the preparation of New Solid Phases (NSP), particularly to amorphous solid phases of sitagliptin as a part of a stable sitagliptin-coformer binary system which presents higher solubility and higher dissolution rate than the sitagliptin salt; wherein the coformers used are derivatives of n-hydroxybenzoic acids.

BACKGROUND OF THE INVENTION

Sitagliptin is commercialized as a phosphate salt and is chemically known as (R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine phosphate monohydrate. This salt has the following structure:

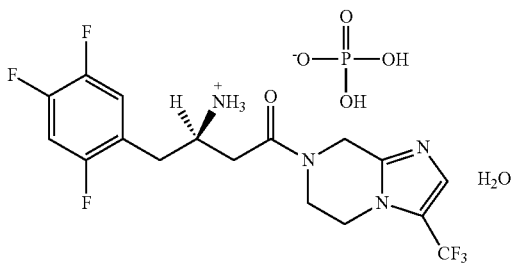

Sitagliptin is a drug used in the treatment of type 2 diabetes mellitus and belongs to the gliptin group. Sitagliptin is a white, crystalline, slightly hygroscopic solid, which is easily manipulated; its structure has a chiral center consisting of a primary amino group.

Its mechanism of action is related with the inhibition of dipeptidyl peptidase (DPP-4), which allows increasing incretin hormones GLP-1 and GIP that control insulin and glucagon release from the pancreas.

On the other hand, the application of crystal engineering has been described as a tool for providing a viable alternative to enhance the physicochemical properties of drugs without modifying their chemical structure. The physicochemical properties of the active pharmaceutical ingredients and the bulk materials can be modified, maintaining the intrinsic therapeutic activity of the molecule (Yadav A., et. al. *Co-Crystals: A Novel Approach to Modify Physicochemical Properties of Active Pharmaceutical Ingredients*, 2009).

The aforementioned is based on the ability of a molecule to exist in two or more solid forms, which differ in the spatial distribution of the atoms or molecules.

As a result of the spatial arrangements of the atoms or molecules, the solids have different physical and chemical properties, which modify the chemical stability, thermal stability, density, hardness, hygroscopic tendency, flow rate, absorption rate (bioavailability) or the behavior of a compound in suspension, and therefore, the final pharmaceutical product.

In the prior art, several crystalline forms of sitagliptin salts, as well as processes for their preparation, have been described. Specifically, document U.S. Pat. No. 6,699,871 B2 describes a process for preparing sitagliptin base and its hydrochloric salt; whereas U.S. Pat. No. 7,326,708 discloses a crystalline form of sitagliptin phosphate monohydrate and a process for preparing the same.

Document EP 2318411 A2 is directed to crystalline salts of sitagliptin with a monobasic, dibasic or tribasic acid, whereas WO 2005/072530 discloses sitagliptin salts and hydrates thereof, wherein the acid addition salt is selected from the group consisting of hydrochloric acid, tartaric acid, benzenesulfonic acid, p-toluenesulfonic acid and 10-camphorsulfonic acid.

WO 2009/085990 and WO 2010/092090 describe crystalline forms of sitagliptin coupled with coformers selected from sulfuric acid, hydrobromic acid, methanesulfonic acid, acetic acid, benzoic acid, oxalic acid, succinic acid, mandelic acid, fumaric acid, D-glucuronic acid, L-lactic acid, malonic acid, citric acid, crotonic acid, ascorbic acid, among others.

WO 2013/054364 A2 refers to solid forms of sitagliptin, particularly to anti-oxidant acid addition salts of sitagliptin, processes for preparing the same, and pharmaceutical compositions containing said salts.

Document US 20140081026 A1 describes a process for the synthesis and industrial production of sitagliptin. In addition, US 20150051213 A1 describes sitagliptin salts with organic acids, polymorphic forms, processes for their preparation and pharmaceutical compositions thereof.

An amorphous solid is the one having particles that lack a long-range order. Amorphous solids constitute a way of increasing bioavailability of poorly soluble drugs by means of enhancing their dissolution rate and solubility (Guy Van Den Mooter, *The use of amorphous solid dispersions: A formulation strategy to overcome poor solubility and dissolution rate*, 2012).

In amorphous solids, the molecular energy is high and molecular mobility is higher than the crystalline state. These features provide unique physicochemical properties to amorphous solids, such as higher solubility and higher dissolution rate in aqueous media (Yihong Qiu, et. al. *Developing Solid Oral Dosage Forms*, 2009).

With regard to amorphous solid phases, document WO 2010/000469 discloses the preparation of an amorphous solid of sitagliptin with citric acid. Document WO 2012/131005 describes pharmaceutical compositions comprising amorphous sitagliptin, wherein the amorphous sitagliptin is prepared from a solution comprising sitagliptin and a crystallization inhibitor selected from cellulose derivates, polyvinylpyrrolidone, polyvinylpyrrolidone derivatives and/or mixtures thereof.

Document US 20140350023 A1 discloses amorphous forms of sitagliptin obtained with mandelic acid, fumaric acid, benzenesulfonic acid, methanesulfonic acid and succinic acid. Document WO 2015/114657 A2 provides amorphous forms of sitagliptin in the absence of coformers.

As mentioned above, the preparation of amorphous solids of sitagliptin has been reported; however, the coformers used in the present invention, as well as the advantages associated to their use, have not been disclosed, aside from the fact that the methods of preparation described in the state of the art are complex.

While amorphous solids possess interesting properties from the pharmaceutical point of view, such as a higher solubility, they are not usually marketed due to their lower chemical stability, higher hygroscopicity and tendency to crystallize.

For the above reasons, there is a need of having new solid phases (NSP) of sitagliptin with enhanced pharmaceutical properties, which are obtained by a simple method and which are also stable under ambient conditions.

BRIEF DESCRIPTION OF THE INVENTION

The present invention describes solid phases obtained from a salt of sitagliptin and a coformer derived from n-hydroxybenzoic acids. N-hydroxybenzoic acids comprise hydroxybenzoic, dihydroxybenzoic and trihydroxybenzoic acids, specifically, the coformers are selected from 2-hydroxybenzoic acid (2-HBA), 3-hydroxybenzoic acid (3-HBA), 4-hydroxybenzoic acid (4-HBA), 2,3-dihydroxybenzoic acid (2,3-DHBA), 2,4-dihydroxybenzoic acid (2,4-DHBA), 2,5-dihydroxybenzoic acid (2,5-DHBA), 2,6-dihydroxybenzoic acid (2,6-DHBA), 3,4-dihydroxybenzoic acid (3,4-DHBA), 3,5-dihydroxybenzoic acid (3,5-DHBA) and 3,4,5-trihydroxybenzoic acid (3,4,5-THBA). The obtained solid phases have different and enhanced physicochemical properties, such as solubility and dissolution rate, as compared to the sitagliptin salt.

BRIEF DESCRIPTION OF THE FIGURES

The following figures are included to illustrate certain aspects of the present invention, and must not be considered as exclusive embodiments.

DETAILED DESCRIPTION OF THE INVENTION

Figure 1:
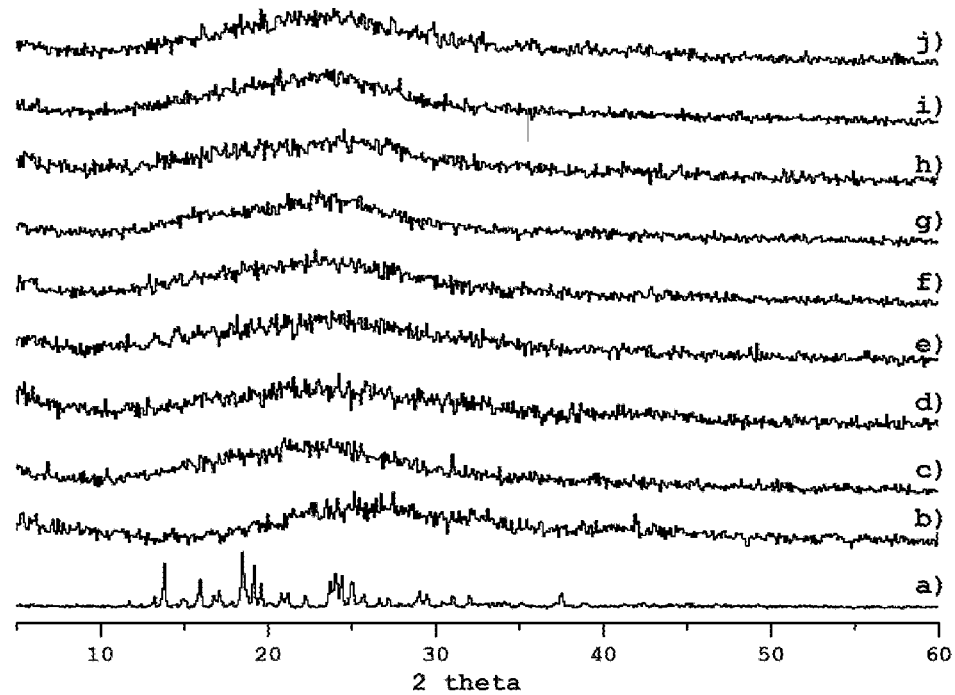
FIG. 1 provides X-ray powder diffraction spectra of: a) crystalline sitagliptin phosphate monohydrate; b) amorphous sitagliptin phosphate monohydrate; c) sitagliptin-3-HBA NSP; d) sitagliptin-4-HBA NSP; e) sitagliptin-2,3-DHBA NSP; f) sitagliptin-2,4-DHBA NSP; g) sitagliptin-2,5-DHBA NSP; h) sitagliptin-2,6-DHBA NSP; i) sitagliptin-3,5-DHBA NSP; and j) sitagliptin-3,4,5-THBA NSP.
Figure 2A:
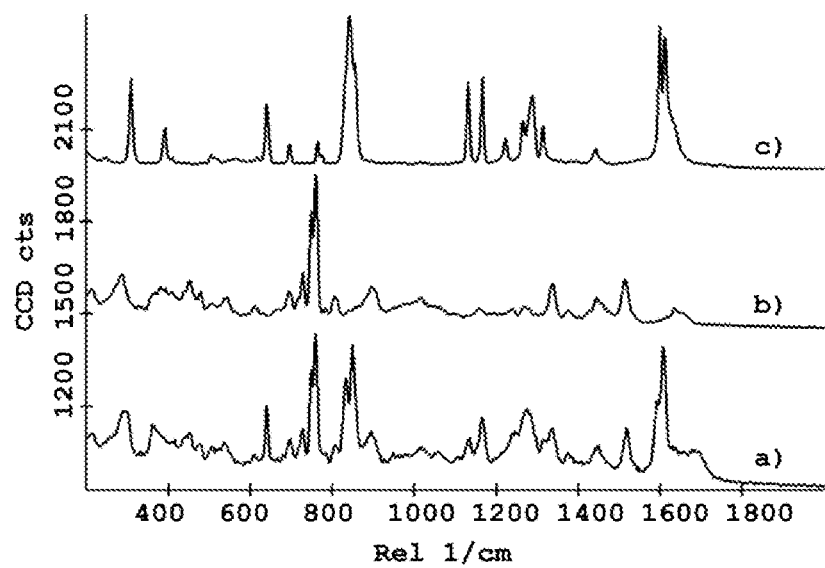
FIG. 2a shows Raman spectra of: a) sitagliptin-3-HBA NSP; b) sitagliptin phosphate monohydrate; and c) 3-HBA.
Figure 2B:
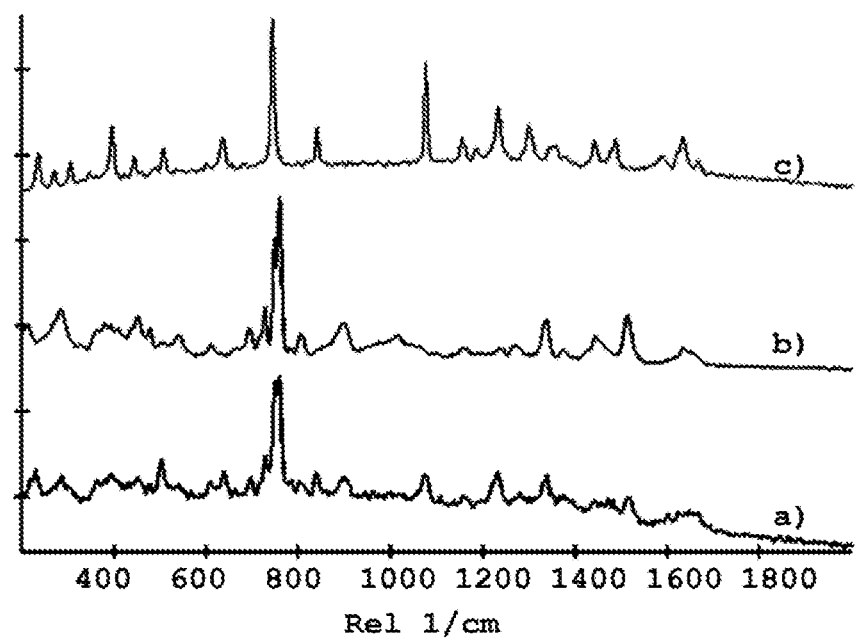
FIG. 2b shows Raman spectra of: a) sitagliptin-4-HBA NSP; b) sitagliptin phosphate monohydrate; and c) 4-HBA.
Figure 2C:
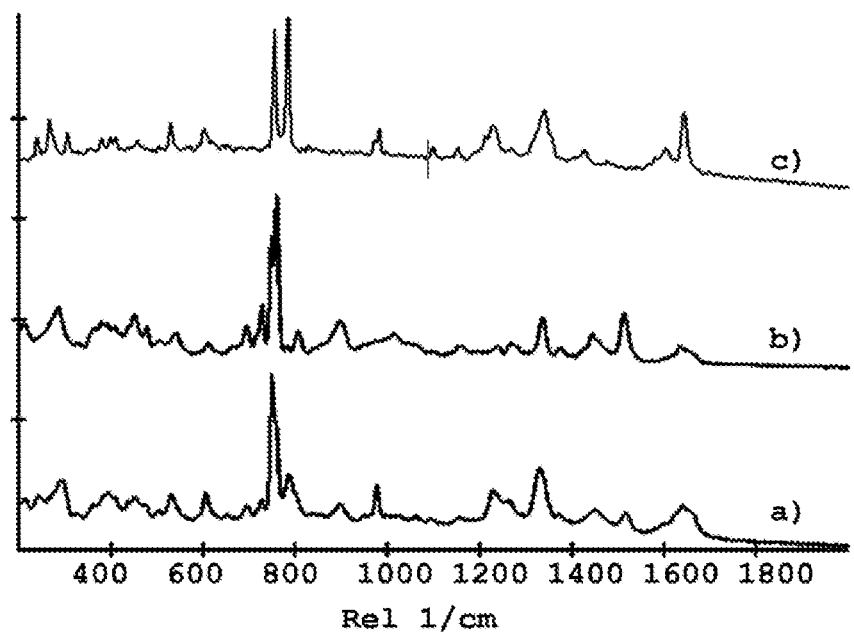
FIG. 2c shows Raman spectra of: a) sitagliptin-2,3-DHBA NSP; b) sitagliptin phosphate monohydrate; and c) 2,3-DHBA.
Figure 2D:
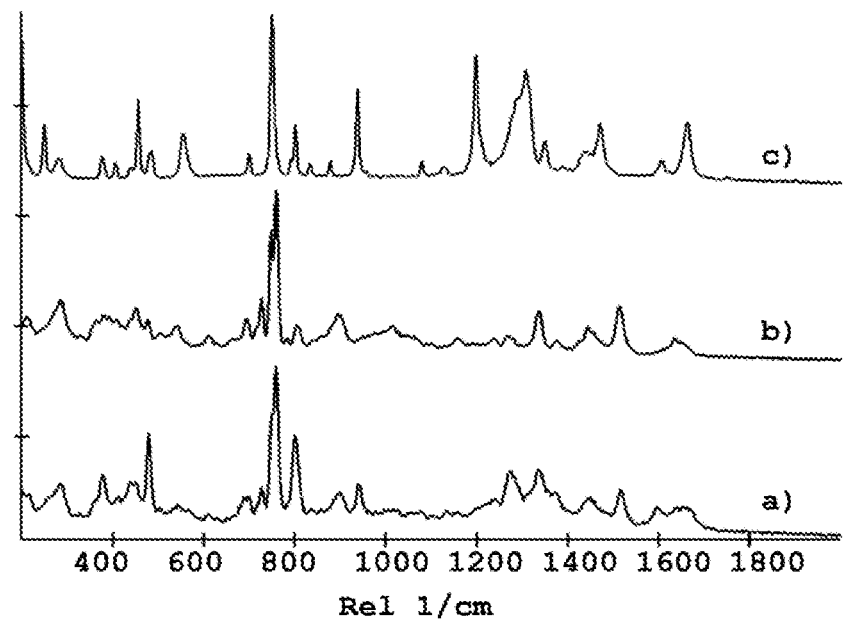
FIG. 2d shows Raman spectra of: a) sitagliptin-2,4-DHBA NSP; b) sitagliptin phosphate monohydrate; and c) 2,4-DHBA.
Figure 2E:
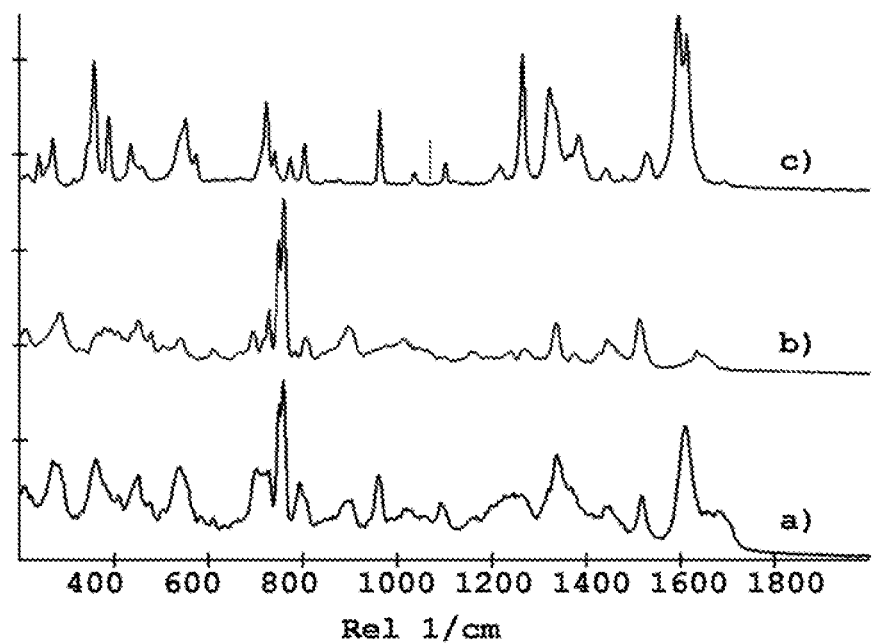
FIG. 2e shows Raman spectra of: a) sitagliptin-2,5-DHBA NSP; b) sitagliptin phosphate monohydrate; and c) 2,5-DHBA.
Figure 2F:
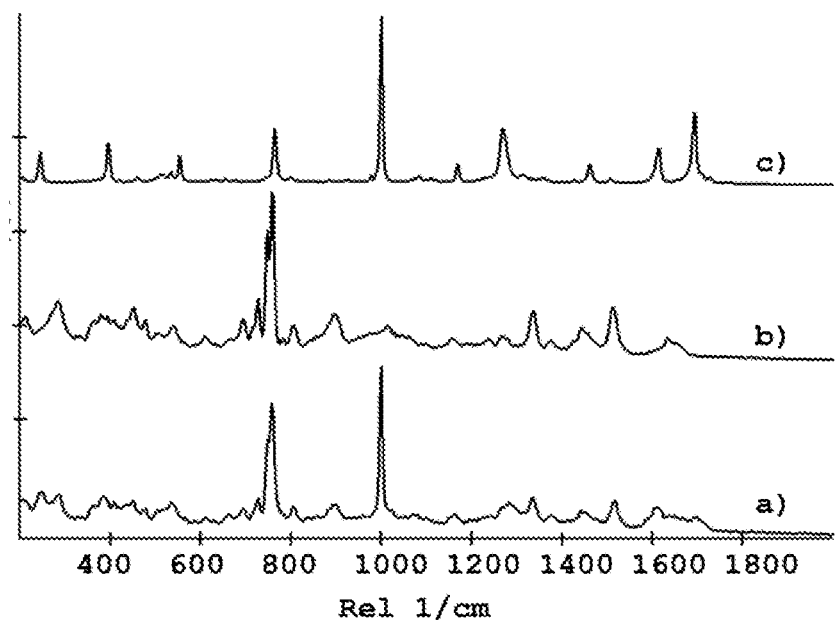
FIG. 2f shows Raman spectra of: a) sitagliptin-2,6-DHBA NSP; b) sitagliptin phosphate monohydrate; and c) 2,6-DHBA.
Figure 2G:
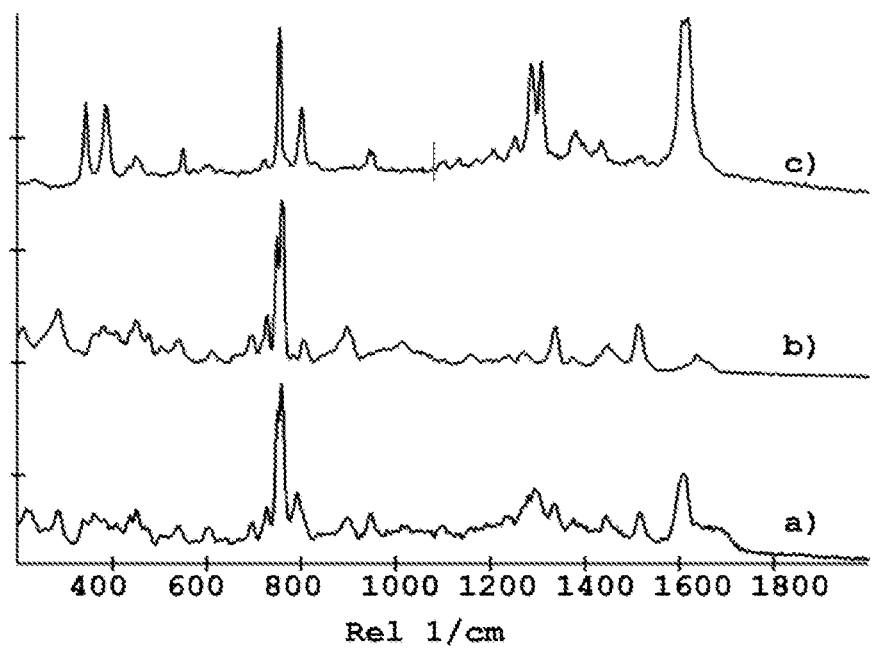
FIG. 2g represents Raman spectra of: a) sitagliptin-3,4-DHBA NSP; b) sitagliptin phosphate monohydrate; and c) 3,4-DHBA.
Figure 2H:
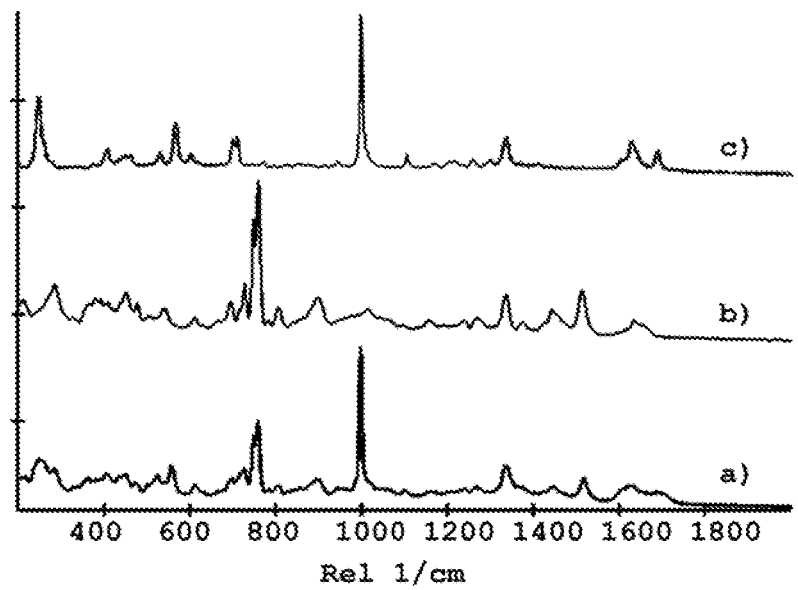
FIG. 2h shows Raman spectra of: a) sitagliptin-3,5-DHBA NSP; b) sitagliptin phosphate monohydrate; and c) 3,5-DHBA.
Figure 2I:
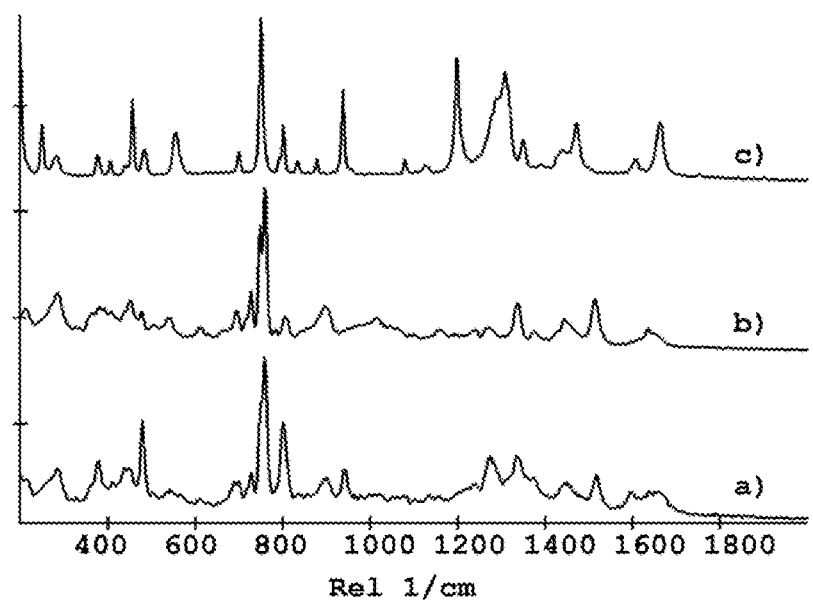
FIG. 2i shows Raman spectra of: a) sitagliptin-3,4,5-THBA NSP; b) sitagliptin phosphate monohydrate; and c) 3,4,5-THBA.
Figure 3A:
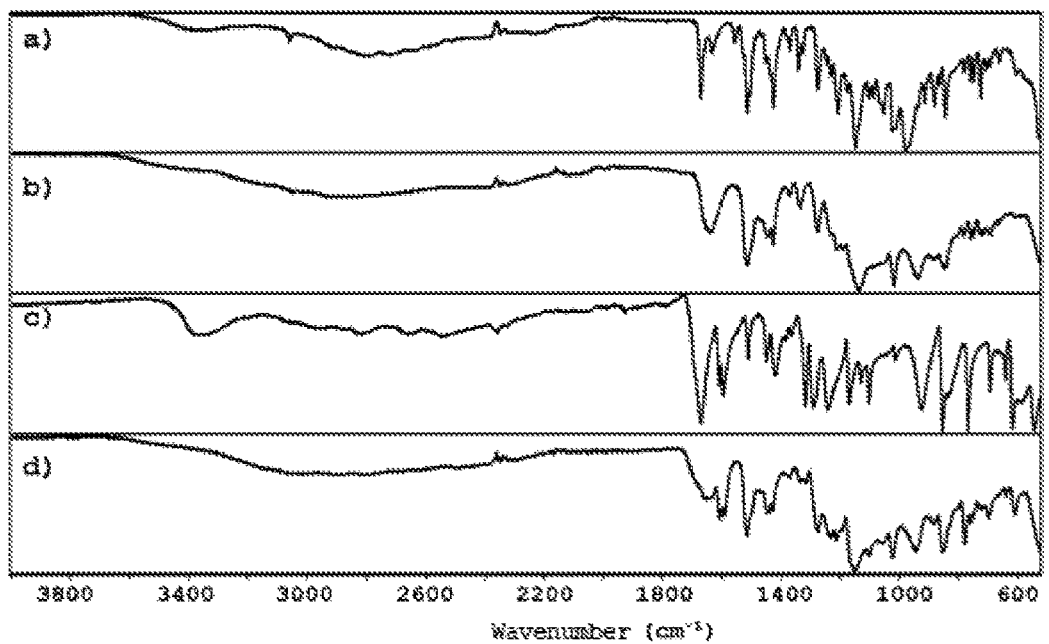
FIG. 3a provides IR spectra of: a) crystalline sitagliptin phosphate monohydrate; b) amorphous sitagliptin phosphate monohydrate; c) 3-HBA; and d) sitagliptin-3-HBA NSP.
Figure 3B:
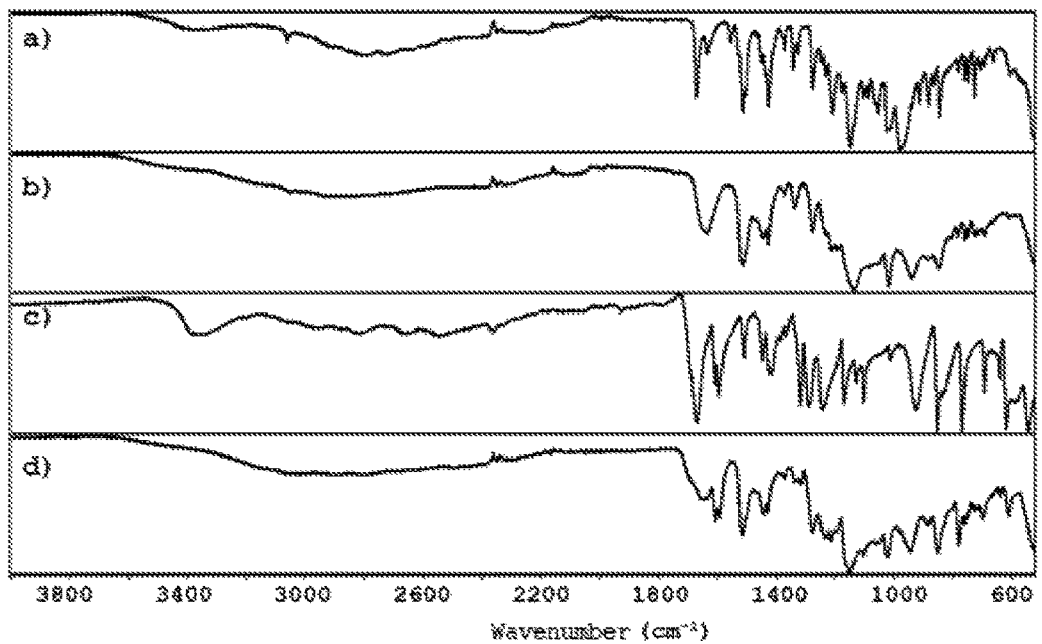
FIG. 3b represents IR spectra of: a) crystalline sitagliptin phosphate monohydrate; b) amorphous sitagliptin phosphate monohydrate; c) 4-HBA; and d) sitagliptin-4-HBA NSP.
Figure 3C:
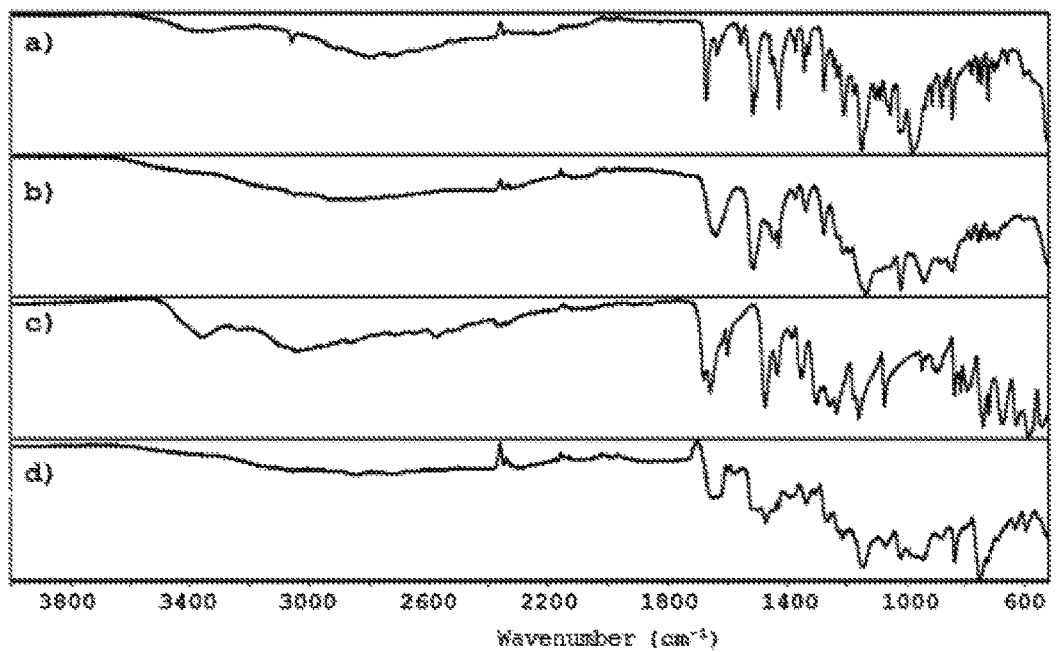
FIG. 3c shows IR spectra of: a) crystalline sitagliptin phosphate monohydrate; b) amorphous sitagliptin phosphate monohydrate; c) 2,3-DHBA; and d) sitagliptin-2,3-DHBA NSP.
Figure 3D:
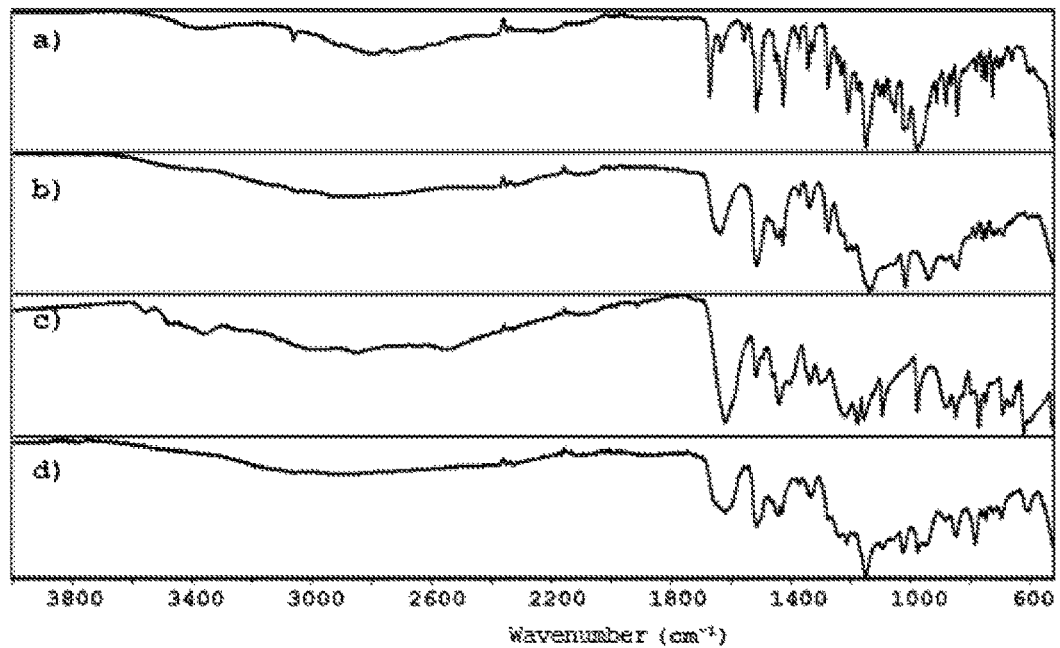
FIG. 3d shows IR spectra of: a) crystalline sitagliptin phosphate monohydrate; b) amorphous sitagliptin phosphate monohydrate; c) 2,4-DHBA; and d) sitagliptin-2,4-DHBA NSP.
Figure 3E:
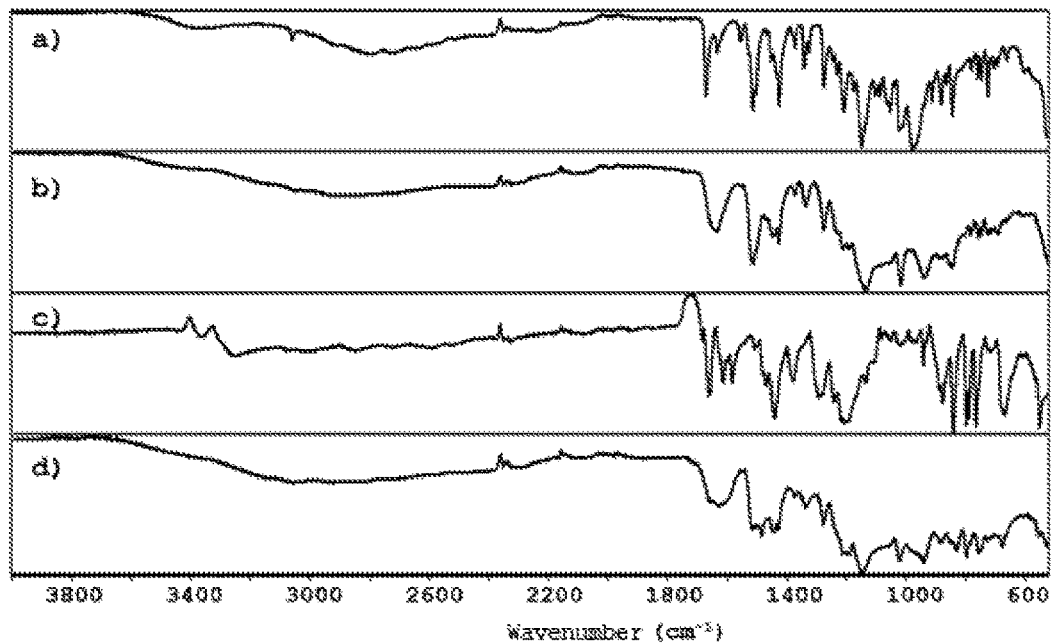
FIG. 3e shows IR spectra of: a) crystalline sitagliptin phosphate monohydrate; b) amorphous sitagliptin phosphate monohydrate; c) 2,5-DHBA; and d) sitagliptin-2,5-DHBA NSP.
Figure 3F:
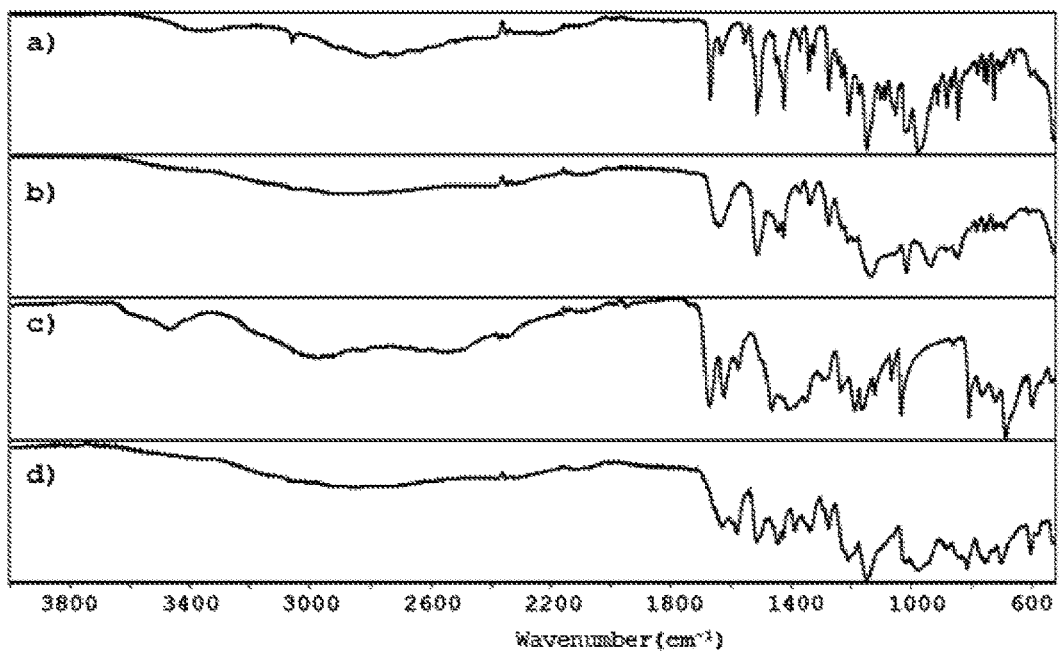
FIG. 3f provides IR spectra of: a) crystalline sitagliptin phosphate monohydrate; b) amorphous sitagliptin phosphate monohydrate; c) 2,6-DHBA; and d) sitagliptin-2,6-DHBA NSP.
Figure 3G:
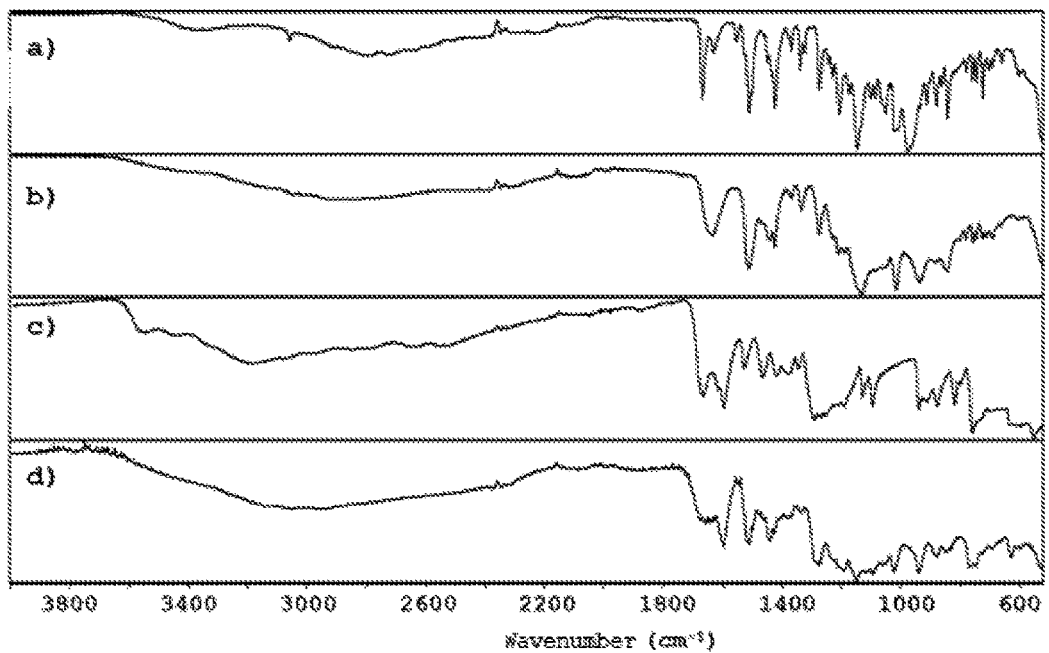
FIG. 3g represents IR spectra of: a) crystalline sitagliptin phosphate monohydrate; b) amorphous sitagliptin phosphate monohydrate; c) 3,4-DHBA; and d) sitagliptin-3,4-DHBA NSP.
Figure 3H:
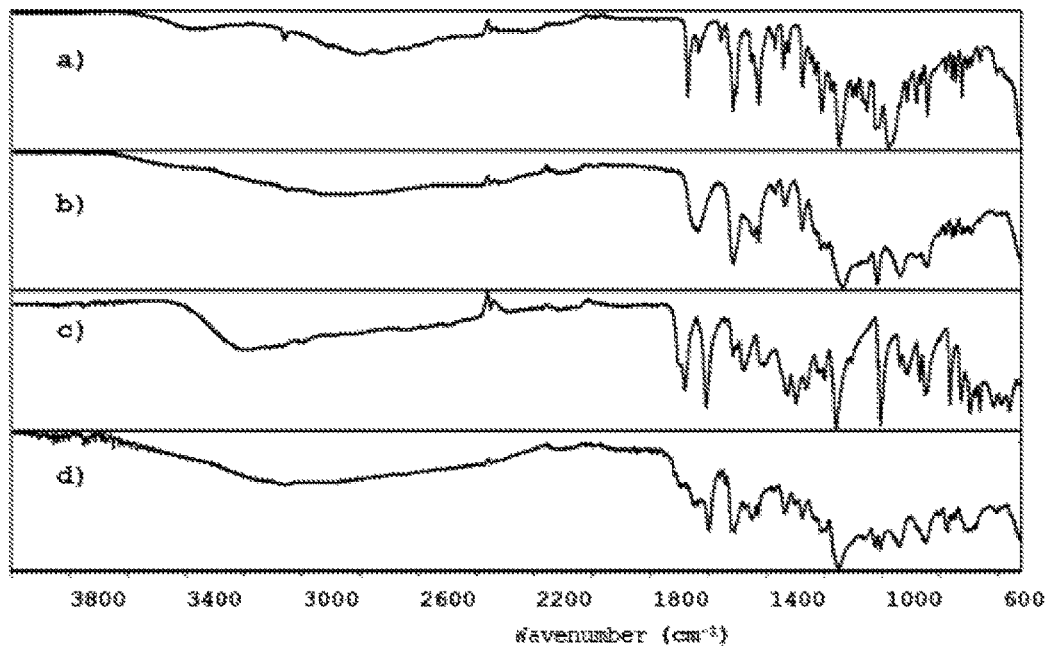
FIG. 3h shows IR spectra of: a) crystalline sitagliptin phosphate monohydrate; b) amorphous sitagliptin phosphate monohydrate; c) 3,5-DHBA; and d) sitagliptin-3,5-DHBA NSP.
Figure 3I:
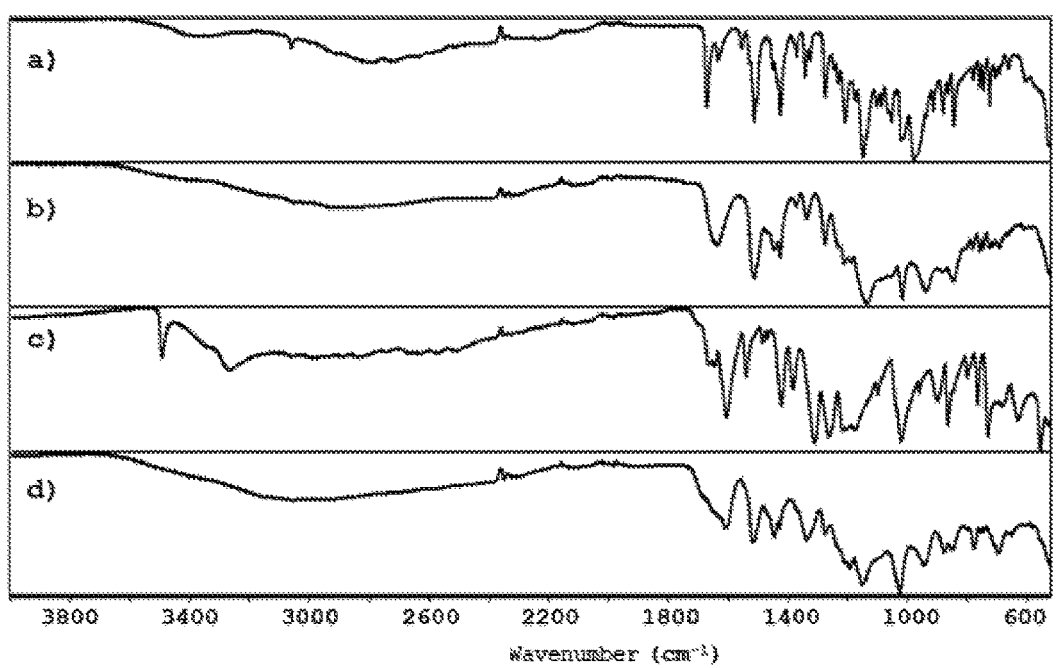
FIG. 3i shows IR spectra of: a) crystalline sitagliptin phosphate monohydrate; b) amorphous sitagliptin phosphate monohydrate; c) 3,4,5-THBA; and d) sitagliptin-3,4,5-THBA NSP.

The present invention provides NSP of sitagliptin with enhanced physicochemical properties, such as higher solubility, dissolution rate, stability and flowability.

As used in the present invention, the term "New Solid Phase" (NSP) refers to a solid phase consisting of a mixture of sitagliptin and a coformer, which interacts with sitagliptin through weak bonds.

The NSP of the present invention are formed from a sitagliptin salt and a coformer, resulting in a sitagliptin-coformer binary system. The obtained NSP are constituted by an aggregate wherein the drug and coformer molecule components do not covalently interact, i.e., they have weak interactions, such as hydrogen bonding, ion pairing or Van der Waals' interactions.

As used in the present invention, the term "coformer" refers to a compound that when combined with the salt of sitagliptin, allows forming a NSP. As described in the present invention, the coformer has only weak interactions with sitagliptin.

In an embodiment, the NSP are formed from the crystalline form of the sitagliptin phosphate monohydrate salt.

The coformers used in the present invention are n-hydroxybenzoic acid derivatives. In one embodiment, n-hydroxybenzoic acids comprise hydroxybenzoic, dihydroxybenzoic and trihydroxybenzoic acids; preferably, 2-hydroxybenzoic acid (2-HBA), 3-hydroxybenzoic acid (3-HBA), 4-hydroxybenzoic acid (4-HBA), 2,3-dihydroxybenzoic acid (2,3-DHBA), 2,4-dihydroxybenzoic acid (2,4-DHBA), 2,5-dihydroxybenzoic acid (2,5-DHBA), 2,6-dihydroxybenzoic acid (2,6-DHBA), 3,4-dihydroxybenzoic acid (3,4-DHBA), 3,5-dihydroxybenzoic acid (3,5-DHBA) and 3,4,5-trihydroxybenzoic acid (3,4,5-THBA) are used. The coformers provide stability to the NSP under ambient conditions.

As described in the present invention, the NSP possess an enhanced dissolution rate, with respect to the sitagliptin salt.

In another aspect, a process is provided for the preparation of the NSP, which process comprises the following steps:
a) Providing a mixture that comprises sitagliptin and n-hydroxybenzoic acid derivative
b) Dissolving the mixture comprising sitagliptin and n-hydroxybenzoic acid derivative in methanol or ethanol
c) Placing the mixture in a rotary evaporator
d) Heating in a 70-85° C. bath under reduced pressure.

As described in the present invention, the mixture of sitagliptin and coformer corresponds to an stoichiometric mixture with a sitagliptin:coformer relationship of 1:1.

EXAMPLES

The following examples have the only purpose of illustrating and demonstrating some embodiments of the invention. The exemplified embodiments must not be considered as limitative for the present invention. As a person skilled in the art will recognize, modifications and variations can be carried out to the embodiments herein described without altering the essence of the invention.

1. Characterization of the NSP

The obtained NSP were characterized by X-ray powder diffraction, Raman spectroscopy and infrared spectroscopy (IR).

a) Characterization of NSP by X-Ray Powder Diffraction

X-ray powder diffraction determines the degree of molecular order in a solid, therefore, it allows distinguishing the presence of crystalline or amorphous solids starting from powder samples. The powder diffractograms of FIG. 1 show diffuse halos without diffraction peaks with respect to the crystalline salt of sitagliptin, which demonstrates a loss of crystallinity, and thus the presence of non-crystalline NSP.

FIG. 1 provides X-ray powder diffraction spectra for: a) crystalline sitagliptin phosphate monohydrate; b) amorphous sitagliptin phosphate monohydrate; c) sitagliptin-3-HBA NSP; d) sitagliptin-4-HBA NSP; e) sitagliptin-2,3-DHBA NSP; f) sitagliptin-2,4-DHBA NSP; g) sitagliptin-2,5-DHBA NSP; h) sitagliptin-2,6-DHBA NSP; i) sitagliptin-3,5-DHBA NSP; and j) sitagliptin-3,4,5-THBA NSP.

b) Characterization of NSP by Raman Spectroscopy

Raman spectroscopy is sensitive to the formation of weak intermolecular forces. FIGS. 2a-2i show a comparison of Raman spectra of the sitagliptin salt, the coformers and the NSP. In these figures, letter a) represents the spectrum of the NSP; letter b) represents the spectrum of sitagliptin phosphate monohydrate; and letter c) corresponds to the spectrum of the coformer.

These spectra show a shifting of the NSP Raman bands, which is indicative of the establishment of intermolecular interactions between the drug and the coformer.

c) Characterization of NSP by Infrared Spectroscopy (IR)

One of the main applications of IR Spectroscopy is the characterization of substances by means of the identification of specific functional groups, especially organic molecules. FIGS. 3a-3i show a comparison of the IR spectra of the crystalline salt of sitagliptin, the amorphous salt of sitagliptin, the coformers and the NSP. In these figures, letter a) represents the spectrum of sitagliptin phosphate monohydrate; letter b) represents the spectrum of the amorphous sitagliptin phosphate monohydrate; letter c) corresponds to the spectrum of the coformer; and letter d) corresponds to the spectrum of the NSP.

Specifically, a loss of definition in the bands is observed with respect to the crystalline salt of sitagliptin, as expected for new amorphous phases.

2. Solubility Tests

Solubility tests are carried out in physiologically relevant media such as hydrochloric acid pH 1.2, acetate pH 4.5, phosphate pH 6.8, and water. A supersaturated solution of the phase is prepared and stirred at 37° C. for 72 h, after such time the mixture is filtered and the filtered liquid is analyzed by UV-Vis spectroscopy; finally, the concentration of the solution is calculated to obtain the dissolved amount (mg).

Due to the high solubility of the NSP, the supersaturation of the solution is not achieved. In an embodiment of the invention, 250 mg of the NSP were added to 200 µL of the solvent, however, it results in the formation of a gel, which solidifies.

3. Dissolution Rate Tests in Aqueous Media.

Figure 4:
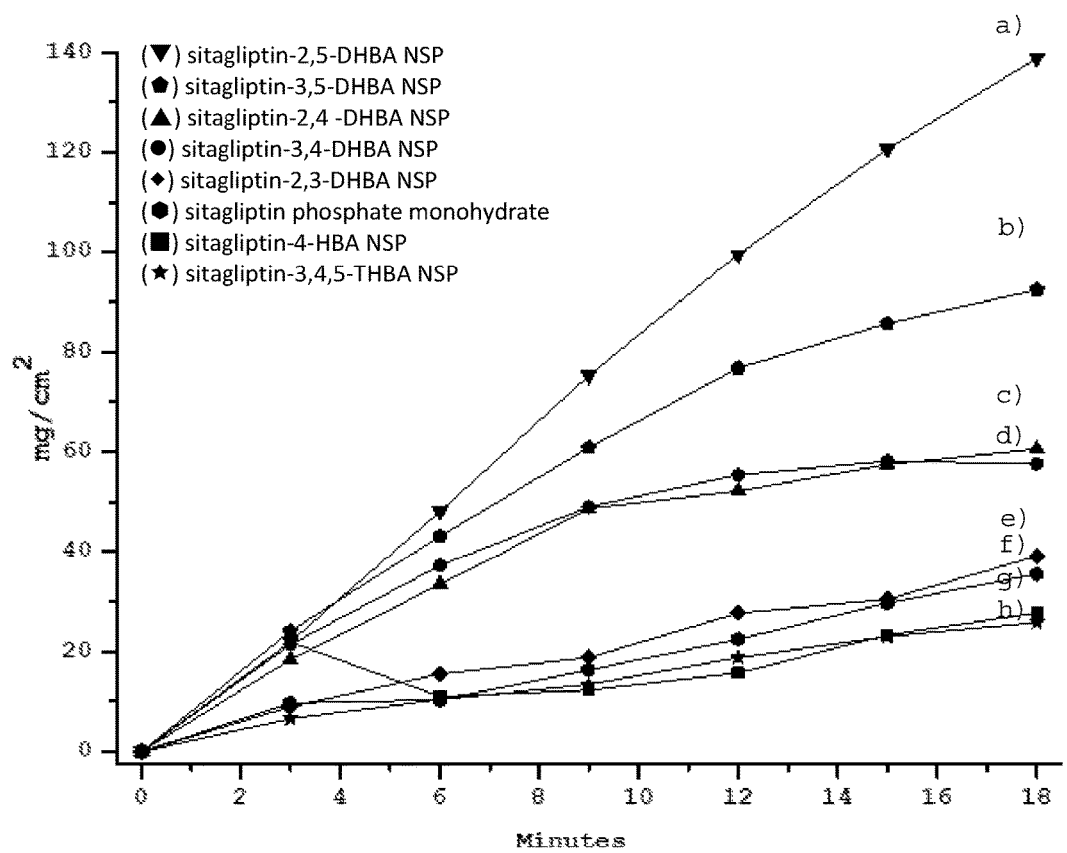
FIG. 4 shows the results of the dissolution rate tests for: a) sitagliptin-2,5-DHBA NSP (▼); b) sitagliptin-3,5-DHBA NSP (◆); c) sitagliptin-2,4-DHBA NSP (▲); d) sitagliptin-3,4-DHBA NSP (●); e) sitagliptin-2,3-DHBA NSP (♦); f) crystalline sitagliptin phosphate monohydrate (◆); g) sitagliptin-4-HBA NSP (■); and h) sitagliptin-3,4,5-THBA NSP (★).

FIG. 4 shows the dissolution profile of the sitagliptin salt, as compared to the NSP. Dissolution rate tests were carried out in water, using a Wood apparatus with 150 milligram tablets, the study was performed at 37° C. and 50 rpm.

NSP exhibit an increased solubility with respect to the sitagliptin salt. In an embodiment of the present invention, a NSP with a solubility increase of up to 400% with respect to the sitagliptin salt, and a dissolution percent of 92.51%, is obtained when the coformer is 2,5-DHBA.

4. Stability Tests

Stability tests are carried out maintaining the NSP at room temperature for a certain time. After such time, visual inspection and X-ray diffraction analysis are carried out to the samples, in order to compare with the spectra obtained at the beginning of the test and to detect a possible change in the NSP.

a) Visual Inspection

In an embodiment of the invention, after a one-month exposure to the aforementioned conditions, the NSP have the aspect of dry foam when the coformer is selected from 3-HBA, 4-HBA, 2,3-DHBA, 2,4-DHBA, 2,5-DHBA, 3,5-DHBA or 3,4,5-THBA.

b) X-Ray Diffraction

Figure 5A:
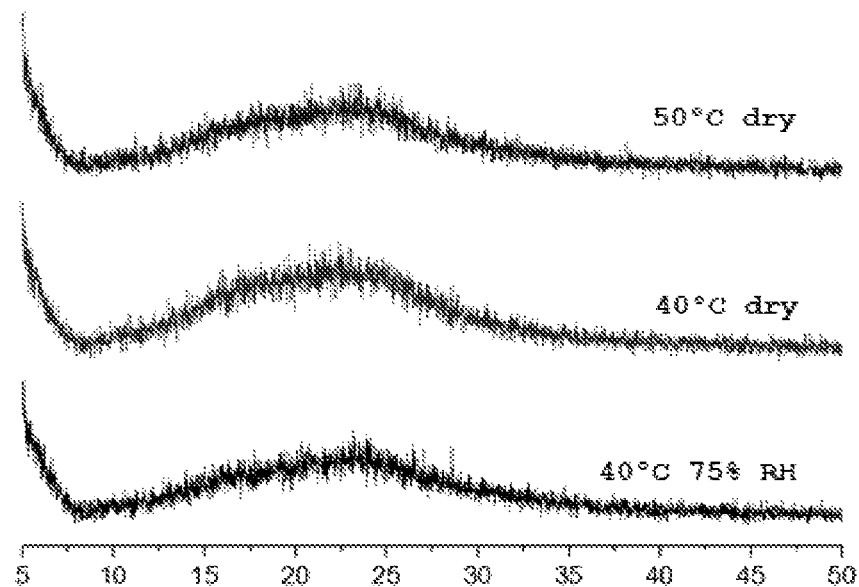
FIG. 5a shows X-ray diffraction spectra of the sitagliptin-3,4,5-THBA NSP in different conditions: 50° C./dry, 40° C./dry and 40° C./75% relative humidity (RH) for a month.
Figure 5B:
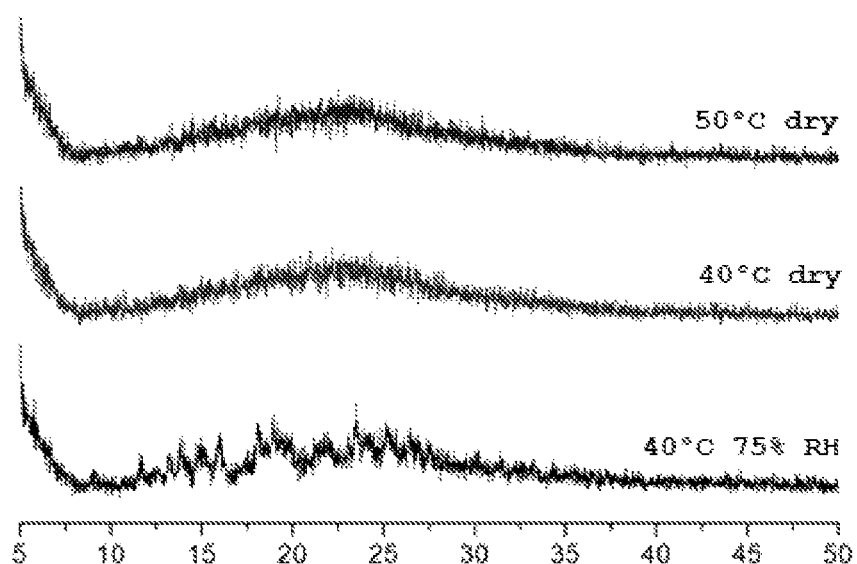
FIG. 5b provides X-ray diffraction spectra of the sitagliptin-3,5-DHBA NSP in different conditions: 50° C./dry, 40° C./dry and 40° C./75% relative humidity (RH) for a month.
Figure 5C:
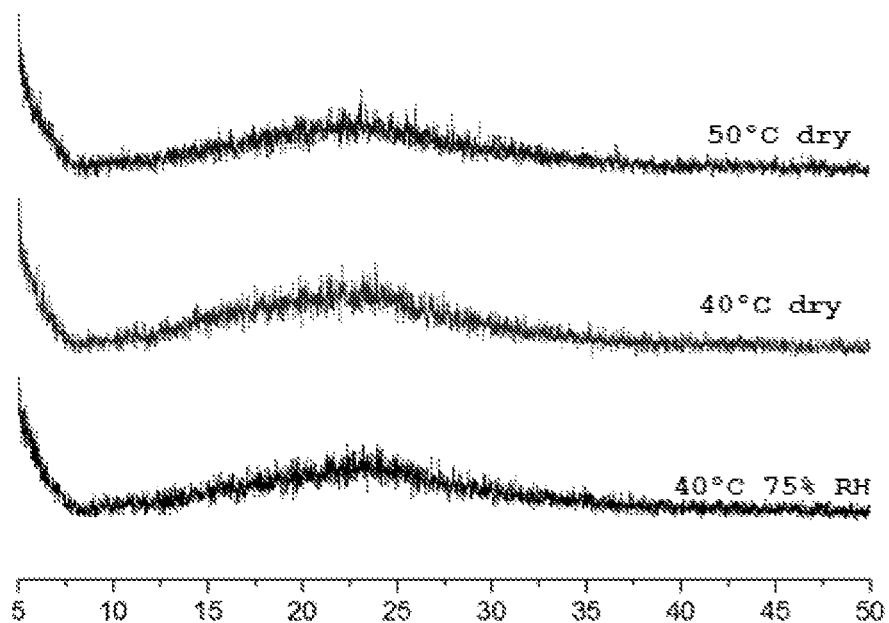
FIG. 5c represents X-ray diffraction spectra of the sitagliptin-2,5-DHBA NSP in different conditions: 50° C./dry, 40° C./dry and 40° C./75% relative humidity (RH) for a month.
Figure 5D:
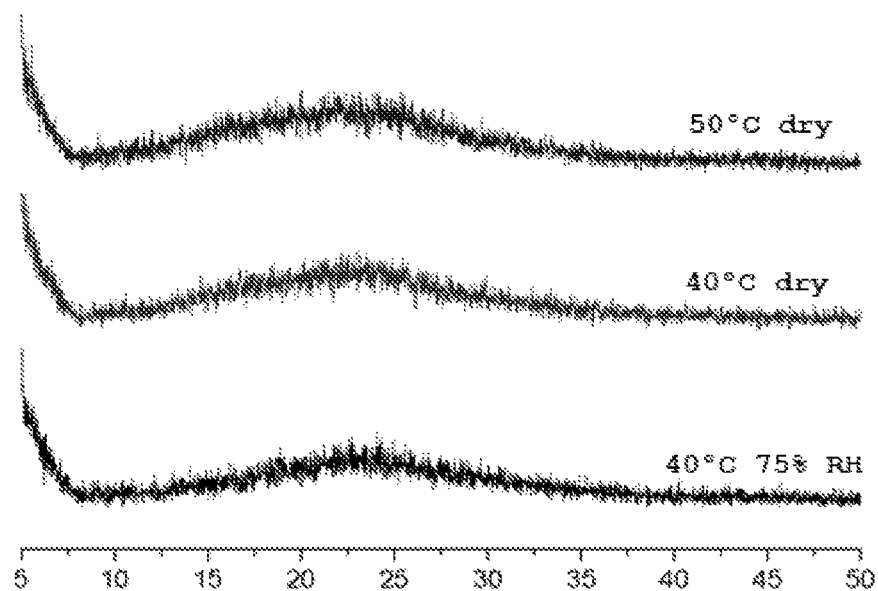
FIG. 5d shows X-ray diffraction spectra of the sitagliptin-2,3-DHBA NSP in different conditions: 50° C./dry, 40° C./dry and 40° C./75% relative humidity (RH) for a month.

FIG. 5b shows that the NSP obtained with coformer 3,5-DHBA presents weak diffraction peaks corresponding to the crystallization of the drug at 40° C. and 75% HR. When the coformer is 2,3-DHBA, 2,5-DHBA, or 3,4,5-THBA (FIGS. 5a, 5c, 5d), the NSP are stable at 50° C./dry 40° C./dry, and 40° C., 75% RH, for one month.

Figure 6:
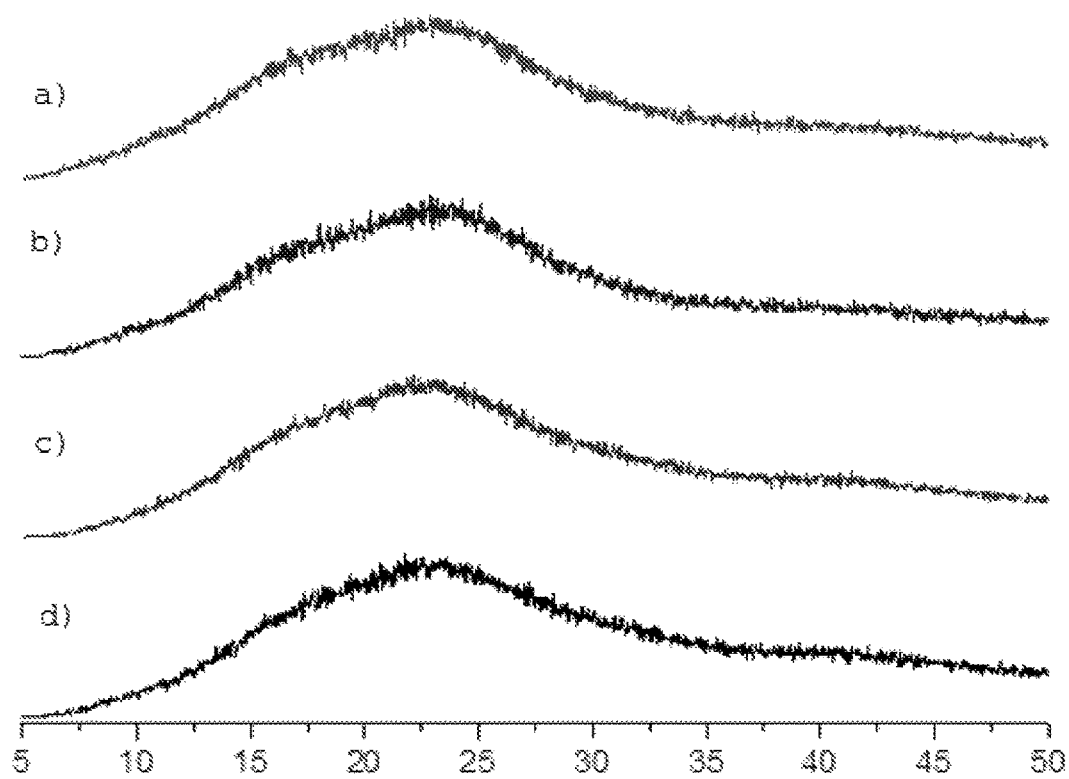
FIG. 6 shows X-ray powder diffractograms of the NSP: a) sitagliptin-2,3-DHBA; b) sitagliptin-2,5-DHBA; c) sitagliptin-3,5-DHBA; and d) sitagliptin-3,4,5-THBA, after one-year storage.

No diffraction peaks indicating the presence of any crystallized component were observed in the X-ray powder diffractograms of the NSP stored for one year at room temperature (FIG. 6). In this sense, the NSP are stable for one year when the coformer is 2,3-DHBA, 2,5-DHBA, 3,5-DHBA or 3,4,5-THBA.

NOVELTY OF THE INVENTION

Having described the present invention as above, it is considered as novel and therefore, it is claimed as a property based on the content of the following:

The invention claimed is:

1. An amorphous solid phase of sitagliptin phosphate salt and a coformer, wherein the coformer is an acid selected from the group consisting of 2-hydroxybenzoic acid, 3-hydroxybenzoic acid, 4-hydroxybenzoic acid, 2,5-dihydroxybenzoic acid, 2,3-dihydroxybenzoic acid, 2,4-dihydroxybenzoic acid, 2,6-dihydroxybenzoic acid, 3,4-dihydroxybenzoic acid, 3,5-dihydroxybenzoic acid, and 3,4,5-trihydroxybenzoic acid.

2. The solid phase in accordance with claim 1, wherein the solid phase is stable under ambient conditions.

3. The solid phase in accordance with claim 1, wherein the solid phase has higher solubility and higher dissolution rate than the sitagliptin phosphate monohydrate.

4. A process for preparing a solid phase of sitagliptin in accordance with claim 1, the process comprising the following steps:
   a) combining crystalline sitagliptin phosphate salt and the acid;
   b) dissolving the mixture comprising sitagliptin and the acid in methanol or ethanol;
   c) placing the mixture in a rotary evaporator;
   d) heating the mixture in a 70-85° C. bath under reduced pressure.

* * * * *